(12) United States Patent
Lacoste et al.

(10) Patent No.: US 11,331,296 B2
(45) Date of Patent: May 17, 2022

(54) PHEROMONE COMPOSITIONS AND USES THEREOF

(71) Applicant: CEVA SANTE ANIMALE, Libourne (FR)

(72) Inventors: Sandrine Lacoste, Carignan de Bordeaux (FR); Alexandra Beck, Saint Martin de Laye (FR)

(73) Assignee: CEVA SANTE ANIMALE, Libourne (FR)

(*) Notice: Subject to any disclaimer, the term of this patent is extended or adjusted under 35 U.S.C. 154(b) by 86 days.

(21) Appl. No.: 16/675,288

(22) Filed: Nov. 6, 2019

(65) Prior Publication Data

US 2020/0069629 A1 Mar. 5, 2020

Related U.S. Application Data

(63) Continuation of application No. 15/748,671, filed as application No. PCT/EP2016/068174 on Jul. 29, 2016, now abandoned.

(30) Foreign Application Priority Data

Jul. 31, 2015 (EP) ................................. 15306249

(51) Int. Cl.
| | | |
|---|---|---|
| *A61K 31/22* | (2006.01) | |
| *A61K 31/19* | (2006.01) | |
| *A61P 43/00* | (2006.01) | |
| *A61K 31/201* | (2006.01) | |

(52) U.S. Cl.
CPC .............. *A61K 31/22* (2013.01); *A61K 31/19* (2013.01); *A61K 31/201* (2013.01); *A61P 43/00* (2018.01)

(58) Field of Classification Search
CPC ..................................................... A61K 31/22
See application file for complete search history.

(56) References Cited

U.S. PATENT DOCUMENTS

2011/0150822 A1* 6/2011 Nouvel ................. A61K 47/12
424/84

FOREIGN PATENT DOCUMENTS

| EP | 0 724 832 | 8/1996 | | |
|---|---|---|---|---|
| GB | 2 345 635 | 7/2000 | | |
| GB | 2345635 A | * 7/2000 | ............. | A61K 9/501 |
| WO | WO 99/37297 | 7/1999 | | |
| WO | WO 2014/001836 | 1/2014 | | |
| WO | WO-2014001836 A1 | * 1/2014 | ............. | A01N 25/34 |

OTHER PUBLICATIONS

He, J. et al. "Distinct Signals Conveyed by Pheromone Concentrations to the Mouse Vomeronasal Organ" *The Journal of Neuroscience*, Jun. 2, 2010, pp. 7473-7483, vol. 30, No. 22.
Seabrook, W. D et al. "Comparison of Electroantennograms from Female and Male Cabbage Looper Moths (*Trichoplusia ni*) of Different Ages and for Various Pheromone Concentrations" *Journal of Chemical Ecology*, Jun. 1, 1987, pp. 1443-1453, vol. 13, No. 6.
Written Opinion in International Application No. PCT/EP2016/068174, Oct. 5, 2016, pp. 1-5.

\* cited by examiner

*Primary Examiner* — Svetlana M Ivanova
(74) *Attorney, Agent, or Firm* — Saliwanchik, Lloyd & Eisenschenk

(57) ABSTRACT

The present invention relates to a composition of less than or equal to about 1% of pheromones useful to treat or prevent a behavioral stress problem of a non-human mammal. It also relates to a device comprising said composition and to a method for preventing and/or treating stress-related behaviors in a non-human mammal, by using said composition or device.

11 Claims, No Drawings

PHEROMONE COMPOSITIONS AND USES THEREOF

CROSS-REFERENCE TO RELATED APPLICATION

This application is a continuation of U.S. application Ser. No. 15/748,671, filed Jan. 30, 2018, which is the U.S. national stage application of International Patent Application No. PCT/EP2016/068174, filed Jul. 29, 2016.

The present invention relates to a composition of pheromones useful to treat or prevent a behavioral stress problem of a non-human mammal. It also relates to a device comprising said composition and to a method for preventing and/or treating stress-related behaviors in a non-human mammal, by using said composition or device.

BACKGROUND OF THE INVENTION

Pheromone therapy, "pheromonatherapy", or "pheromonotherapy" is a way to manage behavior problems in non-human mammals by using chemicals that have pheromonal properties. It is an innovative treatment of stress related problems for non-human mammals, such as non-companion animal species, including pigs and poultry, or domestic animal species, such as cats and dogs. The pheromonatherapy has been studied most extensively in dogs and cats.

Pheromones are chemical substances used for communication between individuals of the same species. Some chemicals that provide interspecies communication are called allelochemicals. Some compounds are known to be a pheromone in one species, but have been observed to have behavioral effects in other species. Pheromones will be used herein in a large sense, i.e. any naturally or non-naturally occurring compound that have a behavioral impact on non-human mammals. The precise mechanism of action of most pheromones is still unknown but they induce some modifications in both the limbic system and the hypothalamus.

Pheromonotherapy is a great way of managing non-human mammals welfare and more particularly some common stress-related behavioral disorders in domestic mammals, such as dogs and cats, without the need for drugs and their associated side-effects.

Pheromonotherapy is successfully used to prevent and/or treat at least one medical or behavioral stress problem of a non-human mammal for pets and especially for cats and dogs.

For cats, Feliway® (Ceva Santé Animale) was the first synthetic version of naturally occurring feline facial pheromones and the first pheromonotherapy used for cat to prevent and/or treat at least one medical or behavioral stress problem. The product mimics the feline's facial pheromones and can be used to calm the pet in stressful situations. When sprayed onto objects in the cat's environment, Feliway® decreases the cat's arousal and stops urine marking and vertical scratching, and other stress-related behaviours. The user always needs to wait for about 15 minutes before letting the cat near any Feliway® sprayed areas, in particular as to let the volatile carrier solvent evaporate.

As this spray schedule may be challenging to comply with, convenient plug-in Feliway® devices have been developed and commercialized by Ceva Santé Animale. These plug-in offer a no-hassle way for pet owners to calm their cats. The pet owner has just to attach the Feliway® source to the plug-in diffuser, plug it into an electric socket in the room most used by the cat, and continue use for four weeks with a liquid plug in diffuser to ensure no relapse in marking behavior.

For dogs, dog appeasing pheromone (DAP® or Adaptil®; Ceva Sante Animale) is a synthetic analog of natural dog-appeasing pheromone that has been promoted as an adjunct treatment to improve conditions such as separation-related behavior problems, loud noise phobias, stress and anxiety. Dog-appeasing pheromone has been reported to reduce separation-induced anxiety, fear in puppies in a new environment and anxiety and stress during transportation. It can also decrease the stress of dogs in public shelter, the training-derived stress of working dogs (police dogs, guide dogs) and the anxiety of puppies in learning and socialization processes. Also, Adaptil® might be a potential treatment for dogs that are fearful of fireworks. Use of Adaptil® in veterinary clinics was significantly associated with greater relaxation in dogs, but did not have an effect on aggression.

Adaptil® is available in two main forms: spray and plug in diffuser.

Adaptil® spray must be sprayed 15 minutes before the dog is introduced into the environment (car, carrier, kennel, etc.), in particular to get the volatile carrier solvent evaporated. Effects should last approximately 4-5 hours and repeated applications can be necessary if the dog owner notice a reduced effect. It is recommended not to spray Adaptil® directly on animals nor near an animal's face. Adaptil® diffuser can be plugged into an electric socket in a room, frequently used by the dog, and continually used for four weeks with a liquid plug in diffuser to comfort both puppies and adult dogs.

Recently, Ceva Santé Animale has introduced Feliway MultiCat® a feline appeasing pheromone to reduce social tension and conflict between cats living in the same home. Feliway MultiCat® pheromone is a synthetic copy of the pheromone produced by a mother cat during lactation. This appeasing pheromone reassures their kittens and helps them bond with the mother. Social tension between cats may impair the cat's day to day welfare. Conflict between cats can begin when a new cat is introduced into the home or previously amicable relationships may change when an event happens that causes one or more cats to become distressed. The cats may have an aggressive encounter and then fail to mend their relationship. Signs of social tension and conflict between familiar cats may be obvious or quite subtle. Overt aggression may include hissing, growling, screaming, hissing, swatting, or chasing. Passive or avoidant behaviors are common too including hiding, fleeing or blocking.

Meridian Animal Health Company launched Nutricalm 24/7 Pheromone Collars for cats and dogs to provide round-the-clock pheromone release. The pheromones in the collars mimic those puppies and kittens are exposed to while nursing and create feelings of security and well-being, even in adulthood.

Perrigo company launched the Sentry® Good Behavior™ pheromone products to reduce and eliminate problems like inappropriate marking, scratching, digging and even pet/owner separation.

Virbac company launched in 2015 a product branded Zenifel® comprising a F3 feline's facial pheromone analogue which can be used to calm the cat in stressful situations. This product contains 10% of pheromone fraction of the total weight for the spray composition and 2% for the plug-in device.

All pheromone products currently available to treat or prevent behavior problems in non-human mammals such as dogs and cats are characterized by a pheromonal fraction around 2 to 10% of the total weight of said composition.

However the prior art does not provide so far an efficient composition comprising pheromones with a low amount thereof. There is a need to develop compositions comprising pheromones at a low amount suitable in a variety of supports and/or useful in a variety of situations, and still effective.

SUMMARY OF THE INVENTION

This present invention relates to a composition comprising pheromones in an amount of less than about 1% by weight with respect to the total weight of said composition.

The composition according to the invention is suitable for a use to treat at least one behavioral stress problem of a non-human mammal, in particular by administration of the composition to said mammal.

Another object of the present invention is a device comprising a composition of the invention, the device being more specifically suitable for a use to treat at least one behavioral stress problem of a non-human mammal.

It also relates to a device comprising said composition and to a method for the treatment of a stress-related behavior in a non-human mammal, by using said composition or device.

DETAILED DESCRIPTION

Definitions

The term «pheromone» as used herein refers to any compound that mimics certain naturally occurring pheromones that have a behavioral impact, such as a calming or appeasing effect, on mammals. It includes any naturally occurring pheromones, said naturally occurring pheromones are one or more secreted compounds by an organism of a specific species which entails a foreseeable reaction (such as for example a calming effect) to another mammal of the same species or another species. As specified earlier, pheromones will be used herein in a large sense, i.e. any naturally or non-naturally occurring compound that have a behavioral impact on non-human mammals. The precise mechanism of action of most pheromones is still unknown but they induce some modifications in both the limbic system and the hypothalamus.

As used herein, the term "about" or "approximately" or "around" will be understood by a person of ordinary skill in the art and will vary to some extent on the context in which it is used. If there are uses of the term which are not clear to persons of ordinary skill in the art given the context in which it is used, "about" will mean up to plus or minus 15% of the particular term.

The percentages are herein expressed by weight, unless otherwise specified.

"Non-human mammals" is intended to mean all animals with the exception of human. The non-human animals include domestic, farm, and zoo animals, including cats, dogs, horses, cattle, tigers, lions, bears, elephants, pigs, boars, etc. According to the present description, when cats or dogs are cited by way of example, it can be generalized to any other domestic, farm, and zoo animals. More specifically, it refers to cats and dogs, and more specifically cats.

According to the invention, the term "comprise(s)" or "comprising" (and other comparable terms, e.g., "containing," and "including") is "open-ended" and can be generally interpreted such that all of the specifically mentioned features and any optional, additional and unspecified features are included. According to specific embodiments, it can also be interpreted as the phrase "consisting essentially of" where the specified features and any optional, additional and unspecified features that do not materially affect the basic and novel characteristic(s) of the claimed invention are included or the phrase "consisting of" where only the specified features are included, unless otherwise stated.

The term "object" or "objects" means any physical thing that can be seen and touched. Examples of objects includes any object that a feline may scratch including, but not limited to, rugs, furniture, carpets, drapes, upholstered corners of couches and chairs, wall papered surfaces, cardboard storage boxes, wood trim on doors and walls. These are only a very few examples defined to encompass the term objects that is used herein. Moreover, feline including cats, may use or uses at least one specific object for scratching (i.e. scratching object), such as cat posts, cat platforms, cat carpets, cat boards, cat toys, cat trees, and the like.

The term «fatty acid», according to the invention, refers to monocarboxylic and dicarboxylic acids with hydrocarbon chains, saturated or unsaturated, linear or branched, liable to have a behavioral impact on stress of non-human mammals. "Derivatives of fatty acids" means all active derivatives of fatty acids. Preferably, the derivatives are in ester (such as methyl ester) or salt forms.

The composition of the invention comprises pheromones in an amount of less or equals to about 1% by weight with respect to the total weight of said composition.

According to a particular embodiment of the invention, pheromones correspond to at least one fatty acid or derivative thereof, more specifically salt or ester thereof, such as methyl ester.

The present invention relates to a composition comprising one or more pheromones, preferably one or more fatty acids or derivatives thereof, as active ingredients, in an amount of less or equal to about 1% by weight with respect to the total weight of said composition, preferably less or equal to about 0.9, 0.8, 0.7, 0.6, or 0.5% by weight with respect to the total weight of said composition. According to a particular embodiment, the composition comprises one or more pheromones, preferably one or more fatty acids or derivatives thereof, as active ingredients, in an amount more than or equal to about 0.3% or 0.4% by weight with respect to the total weight of said composition.

The fatty acids preferably have from 3 to 22 carbon atoms. They can be selected for instance from propanoic acid (propionic), butanoic acid (butyric), pentanoic acid (valeric), hexanoic acid (caproic), heptanoic acid (enanthic), octanoic acid (caprylic), nonanoic acid, decanoic acid (capric), undecanoic acid (undecylic), dodecanoic acid (lauric), tridecanoic acid (tridecylic), pentadecanoic acid, heptadecanoic acid (margaric), octadecanoic acid (stearic), eicosanoic acid (arachidic), arachidonic acid, heneicosanoic acid (heneicosylic), tricosanoic (tricosylic), tetracosanoic acid (lignoceric), pentacosanoic acid (pentacosylic), hexacosanoic acid (cerotic), heptacosanoic acid (heptacosylic), octacosanoic acid (montanic), nonacosanoic acid (nonacosylic), triacontanoic acid (melissic), henatriacontanoic acid (henatriacontylic), dotriacontanoic acid (lacceroic), tritriacontanoic acid (psyllic), tetratriacontanoic acid (geddic), pentatriacontanoic acid (ceroplastic), henatriacontanoic acid (hexatriacontylic), nonanedioic acid (azelaic), oleic acid, y-linoleic acid, palmitic acid, palmitoleic acid, linoleic acid, n-butyric acid, isobutyric acid, [alpha]-methylbutyric acid, tetradecanoic acid (myristic), pentadecylic acid (n-pentadecanoic), heptanedioic acid (pimelic), salt or ester thereof, and a mixture thereof.

According to a specific embodiment, they are chosen among oleic acid, palmitic acid, azelaic acid, pimelic acid, capric acid, myristic acid, palmitoleic acid, linoleic acid, linolenic acid, stearic acid, valeric acid, arachidonic acid, lauric acid, n-butyric acid, isobutyric acid, [alpha]-methyl-butyric acid, pivalic acid, linoleic acid, eicosapentanoic acid, pentadecanonic acid, tridecanoic acid, docosahexanoic acid, salt or ester thereof, and a mixture thereof.

The compositions may comprise at least one fatty acid such as oleic acid, linoleic acid, palmitic acid, valeric acid, a derivative thereof, or a mixture thereof.

By way of examples, we can quote fatty acid mixtures, or their derivatives, ester or methyl ester derivatives, such as:
a mixture of oleic and palmitic acid;
a mixture of oleic and n-butyric acid;
a mixture of valeric and linoleic acid;
a mixture of oleic acid, palmitic acid and linoleic acid;
a mixture of oleic acid, palmitic acid, linoleic acid and palmitoleic acid;
a mixture of capric acid, lauric acid, myristic acid, palmitoleic acid, palmitic acid, linoleic acid and oleic acid;
a mixture of oleic acid, palmitic acid, linoleic acid, myristic acid;
a mixture of oleic acid, palmitic acid, linoleic acid, lauric acid and myristic acid
a mixture of oleic acid, palmitic acid, linoleic acid, myristic acid and pentadecanonic acid;
a mixture of oleic acid, palmitic acid, linoleic acid, myristic acid, pentadecanonic acid and stearic acid;
a mixture of oleic acid, palmitic acid, linoleic acid, myristic acid, lauric acid and pentadecanonic acid;
a mixture of lauric acid, myristic acid, pentadecanonic, palmitic acid, stearic acid, oleic acid, linoleic acid; or
a mixture of oleic acid, azelaic acid, pimelic acid and palmitic acid.

According to a particular embodiment, the composition comprises valeric acid and linoleic acid (or derivative thereof), as pheromones, in an amount of less than or equal to about 1% by weight with respect to the total weight of said composition, preferably less or equal to about 0.9, 0.8, 0.7, 0.6, or 0.5% by weight with respect to the total weight of said composition. Preferably, the amount of valeric acid and linoleic acid (or derivative thereof), as pheromones, is more than or equal to about 0.3% or 0.4% by weight with respect to the total weight of said composition.

The mixture may comprise the above-mentioned fatty acids in appropriate proportions which are well known to any skilled person. By way of example, the mixtures can contain (% are expressed by weight with respect to the total weight of the cited compounds):
about 55-65% of oleic acid and 45-35% of palmitic acid, their derivatives, salts or esters (e.g., methyl ester) derivatives thereof;
about 45% of oleic acid, 16% of azelaic acid, 18% of pimelic acid, and 21% of palmitic acid, their derivatives salts or esters (e.g., methyl ester) derivatives thereof;
about 30% of palmitic acid, 30% of oleic acid, and 40% linoleic acid, their derivatives, salts or esters (e.g., methyl ester) derivatives thereof; or
about 30% of palmitic acid, 40% of linoleic acid, 10% acid palmitoleic and 20% of oleic acid, their derivatives salts or esters (e.g., methyl ester) derivatives thereof; or
about 30% of oleic acid, 20% of palmitic acid, 20% of linoleic acid, 10% stearic acid, 5% pentadecanoic acid, 5% myristic acid and 2% lauric acid, their derivatives, salts or esters (e.g., methyl ester) derivatives thereof;
about 10% of valeric acid and 90% of linoleic acid, their derivatives, salts or esters (e.g., methyl ester) derivatives thereof.

According to an embodiment of the present invention, the pheromones used herein are compounds to treat or prevent a behavioral stress problem of a non-human mammal, more particularly either cats or dogs, preferably cats.

According to a particular embodiment of the present invention, the fatty acid mixture comprises a mixture of appeasing fatty acids for cats. Preferably, this mixture comprises at least a therapeutically effective amount of active fatty acids, derivatives thereof, salt or ester thereof and preferably chosen among lauric acid, myristic acid, stearic acid, linoleic acid, oleic acid, valeric acid, azelaic acid, pimelic acid, palmitic acid, and a mixture thereof. The mixture of fatty acids preferably comprises linoleic acid and valeric acid.

According to another embodiment of the invention, the mixture comprises a mixture of fatty acids that are appeasing for dogs. Preferably, this mixture comprises a therapeutically effective amount of fatty acids, their derivatives, salt or ester thereof. These are preferably chosen among lauric acid, myristic acid, pentadecanoic acid, palmitic acid, stearic acid, oleic acid and linoleic acid. By way of example, a mixture of ester fatty acids for dogs comprises about 35% of methyl oleate, about 2% of methyl laurate, about 13% methyl stearate, about 21% methyl linoleate, about 5% methyl myristate, about 4% methyl pentadecanoate, and about 20% methyl palmitate.

According to a preferred embodiment, the composition further comprises lactic acid or an ester thereof, such as methyl or ethyl lactate.

In a more preferred embodiment, the composition further comprises ethyl lactate. According to a specific embodiment, the composition comprises valeric acid, linoleic acid and ethyl lactate. Ethyl lactate is preferred since it seems less degraded during storage than its acid form. The mixture of valeric acid, linoleic acid and ethyl lactate is in appropriate proportions which are preferably about 75-85% of linoleic acid, 5-15% of valeric acid, and 10-20% of ethyl lactate (% are expressed by weight with respect to the total weight of the cited compounds).

The composition of the invention can be formulated in any form such as a powder, spray, liquid, gel or aerosol, having components known to those skilled in the art. In a particular embodiment, the composition further comprises an acceptable carrier. Said acceptable carrier includes compounds well known to one of skill in the art and comprises excipients and auxiliaries which facilitate processing of the pheromones into preparations which can be used for non-human mammals. Further details on techniques for formulation and administration may be found in the latest edition of "Development and Formulation of Veterinary Dosage Forms" edited by Gregory E. Hardee and J. Desmond Baggot (1998).

Generally, the pheromone based composition is in a solution form (from oily to liquid phases). The composition of the present invention preferably comprises at least one solvent. The solvent includes glycols, such as propylene glycol, diethylene glycol, glycol ethers (e.g., mono- or di-alkyl ethers of ethylene glycol), such as ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether, diethylene glycol mono-n-butyl ether, ethylene glycol dimethyl ether, ethylene glycol diethyl ether, ethylene glycol dibutyl ether, and the like. The solvents may also be selected from alcohol (such as ethyl alcohol, propyl alcohol, isopropanol, 2-propanol), ether, chloroform, benzene, acetone, volatile oils and the like.

More generally, the active ingredients may be combined with any solid or liquid additives corresponding to the usual techniques of formulation development. The composition, for instance, may also comprise at least one volatile organic compound, including, but not limited to, ketones, such as acetone, alcohols, sterols and the like. The composition may also comprise coloring agents. The composition may also comprise at least one antioxidant. Examples of antioxidants include without limitation, sulfate compounds, L-cysteine, thiodipropionic acid, thiolactic acid, monothioglycerol, propyl galate sodium metabisulfite, sodium formaldehyde, sulfoxylate acetate, butylated hydroxyanisole (BHA) and butylated hydroxytoluene (BHT), vitamin E, ascorbic acid (vitamin C), vitamin B12, or a combination of these agents. The antioxidants, such as BHT, may be present in the composition described herein in an amount of 0.001% to 0.1% by weight with respect to the total weight of said composition. The antioxidants, such as BHT, can also be present in the amount of 0.005% to 0.015% by weight with respect to the total weight of said composition, preferably 0.01%.

Cat attractants can also be optionally added to the composition. These include catnip (*Nepeta Cataria*), essential oil of catnip, tatarian honeysuckle (*Lonicera tartarica*), Valerian (*Valerriana officicinalis*), silver vine/matatabi (*Actinidia polygama*), cat thyme (*Teucrium maxum*), Buckbean (*Menyanthes trifoliate*), actinidine, actinidiolide, boschnialactone, boschniakine, dihydroactinidiolide, dihydronepetalactone, epinepetalactone, iridomyrmecin, isodihydronepetalactone, missugashiwalactone, neonepetalactone, onikulactone and mixtures thereof. The cat attractants may be present in the composition described herein in an amount of 0.02% to 0.20%, preferably 0.05% to 0.15%, by weight with respect to the total weight of said composition. They can also be present in the amount of 0.01% to 0.10% by weight with respect to the total weight of said composition, preferably 0.1%.

Additional components may optionally be included such as, but not limited to, plasticizers, fragrances, coloring agents, preservatives, light stabilizers, and the like.

An object of the invention is a use of the composition as defined herein to prevent and/or treat of at least one behavioral stress problem of a non-human mammal, in particular by administration of the pheromones based composition to said non-human mammal. The administration of the pheromones based composition to a non-human mammal can be made directly or indirectly.

The composition of pheromones according to the invention can be administered to a non-human mammal by propelling or applying the composition onto, over or nearby the non-human animal or a part thereof. The method of administration of the composition according to the invention can be implemented in a place where a non-human mammal is located. The place can be of any kind, such as for example a confined place, for instance a car, truck, carrier, small house or kennel. For cats, the pheromones-based composition can also be applied to any scratching object in which the cat has or may have a tendency to scratch, such as cat posts, cat platforms, cat carpets, cat boards, cat toys, cat trees, and the like. This can help the cat not to scratch somewhere else.

According to a particular embodiment, the invention relates to a method for preventing a cat from scratching on multiple objects, said method comprising placing at least one composition of the invention on a scratching object (i.e.: an object dedicated for scratching).

The administration onto a non-human mammal or a part thereof or the application on an object can be carried out by propelling, spraying, applying or diffusion of the composition of pheromones depending on the forms (solution, solid . . . ) of the composition.

The amount of pheromones to be administered according to the invention varies and depends for instance on the nature of pheromones and the non-human mammal but it should be sufficient to prevent and/or treat behavioral stress problems of a non-human mammal. In a specific embodiment, the effect should be obtained immediately, e.g. within less than 10 minutes, more preferably less than 5 minutes. The administration can be renewed, one, two or three times, if no satisfactory effect is obtained or if reduced effect is observed.

The composition of pheromones as defined above is particularly effective to prevent and/or treat at least one behavioral stress problem of a non-human mammal.

More particularly, the composition of pheromones according to the present invention can prevent territorial urinary marking and/or familiarize the animals with a new environment, and/or prevent noisy outbursts, soiling, destructions, scratching, stamping in the territories or aggressiveness.

The administration of the composition of pheromones may take place over very short periods of time, such as for example during traveling periods, or, on the contrary, can be repeated whenever necessary depending on the animal behavior. It can be renewed if necessary according to stress behaviors of the non-human mammals.

According to a particular embodiment, the administration or application is repeated once a day for two or more days, such as 3, 4, 5, 6, 7, or 8 days, then the frequency of administration can be diminished, such as once weekly for one, two, three or four more applications, to achieve behavioural changes (as to manage for instance cat's scratching behaviours).

The composition according to the present invention is particularly efficient on canine and feline and more especially on dogs and cats.

Behavior stress origins for dogs today could be found for example in the owners' hectic lifestyles difficult to cope with, because owners are constantly on the go whether it be moving house, going on holiday, having parties and even loud noises people make for fun like fireworks night. Accordingly, behavior stress signs increases such as for example excessive barking, agitation, trembling, shaking, shivering, drooling/salivating, cowering and hiding, licking, scratching, yawning, clinging to owners, trying to run away/ attempting to escape, soiling the place, excessive pacing and panting, refusing to eat, vomiting, whining, urinating/defecating, or any combination of said signs.

Cats, unlike dogs, are considered to be territorial animals. They have very specific behaviors centralized around their territory. Only when their environment is secure will some cats develop a relationship with other pets or humans. Stress origins for cats can be for example multi-cat households, visiting the vets, moving home, new house furniture and redecorating, cat carrier . . . . The behavior stress signs in cats can be illustrated for example by scratching, urine marking, aggression, food intake disorders (over-feeding), overgrooming (bald areas) or undergrooming (matted or soiled fur), house soiling, decreased levels of activity, appearing withdrawn (reduced desire to play or interact to owners), or any combination of said signs.

The compositions, mixtures, uses and methods according to the present invention thus allow preventing and/or treating at least one behavioral stress problem of a non-human mammal. For example, repetitive urinary markings of cats occurring in case of stress of cats due to circumstances or particular changes to their immediate environment. It also allows the improvement of the conditions for the non-human mammals to familiarize themselves with their new environment, especially during travels, and/or to prevent stamping and territorial destructions, and/or reduce noisy outbursts. The compositions, and mixtures according to the present invention are thus intended to be used in circumstances where, for instance, a dog or a cat has shown, or is anticipated to show, signs of stress when being transported in a car.

For cats, the beneficial effects can be measured for example by the reduction of the urinary markings and by the repeated physical contact or rubbing against new objects and people that surround them. According to a specific embodiment, the composition of pheromones according to the present invention when applied on a scratching object allows orientation or reorientation of the cats to said object, and consequently prevents a cat from scratching on multiple objects. On the whole, the composition of pheromones according to the present invention allows the improvement of behavior of the non-human mammals in their environment and people present in that environment, with a notable reduction of stress, urinary marking and/or noisy outbursts, as well as behavior that is non aggressive and more relaxed and more affectionate, especially with their owners.

The composition of pheromones according to the invention may be administered by any means or devices suitable for administration, preferably in ambient temperature, of said composition to a non-human mammal or a part thereof or to any object that a non-human mammal has or may have the habit to touch or scratch.

The present invention also deals with a device comprising a composition of the invention, preferably the device presents means for the release of the composition of pheromones. The device may also comprise means to apply, propel, diffuse or spray the said composition.

In ambient air the composition of pheromones preferably presents itself under a liquid or a gel form.

The said device may be, for example, a container, such as a bottle, with a spraying means. A kit comprising a device may also be envisaged, the said kit comprising a device, in particular at least one container or a number of containers, such as vials, a composition as defined in the present invention, and optionally a booklet giving instructions to use said device. The said device may be in ready-to-use form, i.e. prefilled, or may need to be filled before use.

An object of the invention is a use of the composition or kit as defined herein to treat or prevent a behavioral stress problem of a non-human mammal.

According to a specific embodiment, the kit comprises at least one vial comprising the composition of the invention and optionally a booklet giving instructions to use said at least one vial.

The device or kit according to the invention is suitable for a use to prevent and/or treat of at least one behavioral stress problem of a non-human mammal, in particular by administration of the pheromones-based composition comprised therein to said non-human mammal or by application of the pheromones-based composition comprised therein on an object, as detailed above.

The present invention will be better understood in view of the Examples below.

EXAMPLES

Formulas
Formulas of the compositions according to the invention are detailed in Table 1 below. They were prepared by mixing of the ingredients.

TABLE 1

| Compounds | Formula A (g) | Formula B (g) |
| --- | --- | --- |
| Valeric acid | 0.0425 | 0.0425 |
| Ethyl lactate | 0.0625 | 0.0625 |
| Linoleic acid | 0.395 | 0.395 |
| Coloring agent (black E151) | 0.0200 | 0.0200 |
| Catnip oil | 0.1000 | 0 |
| Valeriana | 0 | 0.1000 |
| BHT/BHA | 0.0300 | 0.0300 |
| Propylene glycol | qsp 100 | qsp 100 |

100 g of formula A corresponds to 96 mL.

Stability Tests

Stability of Formula A was tested over a 7 month-period in a white glass flask and carried out under two controlled temperature and humidity conditions (40° C. and 75% Relative Humidity (RH) or 25° C. and 60% RH). Detection and measures of the valeric acid, ethyl lactate and linoleic acid were made by using Gas chromatography (GC).

Methods:

1. Standard Solution

Approximately 490 mg of linoleic acid, 53 mg of valeric acid and 78 mg of ethyl lactate accurately weighed are introduced into a 50 ml volumetric flask. This is completed to volume with ethyl acetate. The solution is stirred for at least 10 minutes. A dilution 1/20 is made and completed to volume with ethyl acetate and the solution is stirred to homogenize.

2. Sample Preparation:

Approximately 2.5 g of Formula tested is introduced into a 20 ml volumetric flask. This is completed to volume with ethyl acetate. The solution is stirred for at least 10 minutes and filtered through 0.45 μm filter. The solution is limpid.

3. Chromatographic Parameters:

Gas chromatography equipped with a Capillary Column HP-FFAP 25 m×320 μm and a FID detector at 250° C. 1 μl of the solution is injected in the inlet (250° C.) and eluted through the column with Helium at constant flow (3 ml/min).

Results:

Valeric acid (≈5.2 min), linoleic acid (≈13.5 min) and ethyl lactate (≈2.7 min) are quantified and contents thereof (% w/w) are given by the ratio of the areas of the peak corresponding to valeric acid, linoleic acid or ethyl lactate in the chromatogram obtained with the sample preparation and the standard solution.

Results at 3 and 7 months are given in Table 2.

TABLE 2

| Compounds | T0 month (% w/w) | T3 months (40/75) | T3 months (25/60) | T7 months (25/60) |
| --- | --- | --- | --- | --- |
| Valeric acid | 0.0425 | 0.038 | 0.039 | 0.039 |
| Ethyl lactate | 0.0625 | 0.059 | 0.060 | 0.059 |
| Linoleic acid | 0.395 | 0.364 | 0.386 | 0.398 |
| Total of the fraction | 0.425-0.575 | 0.461 | 0.485 | 0.496 |

Formula A is stable and is in compliance with the target concentration specifications (±15%).

Efficiency Tests

A trial was made to assess the efficacy of formula A on 173 cats that were redirected to new households and on 38 newly adopted cats. Evaluation was made on the efficacy of formula A in managing/moderating/preventing undesired vertical cat scratching behaviors.

Protocol

The perceived efficacy of the formula A-treated scratch-post was evaluated over a 4-week period of use.

All participants (cats' owners) are male or female, aged 18+, own a cat or kitten for which they have full or shared responsibility; and which is currently healthy (i.e. no major disease, nor undergoing any treatment), have no more than two cats in their household, have cats which do not have lesions on the feet, pain in the limbs or back, have cats which are not declawed, have not participated in any research about cat scratching in the home, which involved applying a product to a scratch post, have not used any pheromone products within the last 4 weeks to manage or prevent cat behavioural problems, have not used any medications within the last 3 months to manage or prevent cat behavioural problems.

All participants in redirected cat households have experienced unwanted or troublesome vertical scratching by their cats in home, such as on fabrics, furniture, carpeted stair-risers, within the last year. 54% of redirected households currently had at least one scratch post before trial.

All participants in newly adopted cat households did not currently own scratch post and have a newly adopted cat which had been introduced into their household less than 2 weeks before commencing the product trial.

The product is the liquid formula A as defined above. The formula is in a small plastic squeeze tube (5 mL) to be applied in a vertical line on a dedicated scratch post.

This process is repeated once a day for 7 days then once weekly for 3 more applications.

10 tubes are furnished to the participants in a pack. 10 applications were made, one for each of 7 consecutive days and three follow-up applications to be used once every 7 days until used up (i.e. total usage period of one month).

Results

More than three quarters (about 80%) of cats in redirected households had started to use the newly provided scratch post at Day 7.

At Day 28, around 9 out of 10 cats in redirected households had used the scratch post (in some capacity) since its introduction into the home.

Nearly all (33 out of 38) newly adopted cats had started to use the newly provided scratch post at Day 7.

At Day 28, all newly adopted cats had used the scratch post (in some capacity) since its introduction into the home.

Moreover, 41% of cats in redirected households had started to use the newly provided scratch post within the first 15 minutes and 74% of newly adopted cats had started to use the newly provided scratch post within the first 15 minutes after first application of the product.

We claim:

1. A composition comprising ethyl lactate and a mixture of pheromones, wherein said mixture of pheromones is present in an amount of less than or equal to about 1% by weight with respect to the total weight of said composition and said mixture of pheromones is a mixture of fatty acids of linoleic acid, salts, or esters thereof and valeric acid, salts, or esters thereof.

2. The composition according to claim 1, wherein the mixture of pheromones is present in an amount between about 0.3% and about 0.9% with respect to the total weight of said composition.

3. The composition according to claim 1, wherein the mixture of pheromones is present in an amount of less than or equal to about 1% by weight with respect to the total weight of said composition and the mixture of pheromones is about 10% valeric acid, salts, or esters thereof and about 90% linoleic acid, salts or esters thereof.

4. A method for the treatment of a behavioral stress problem of a non-human mammal, comprising the administration to said non-human mammal a composition as defined in claim 1.

5. The method according to claim 4, wherein the composition is administered to a non-human mammal by propelling or applying the composition onto, over or near the non-human animal or a part thereof.

6. The method according to claim 4, wherein the non-human mammal is a canine or feline.

7. The method according to claim 6, wherein the non-human mammal is a dog, and the behavioral stress problem is a stress sign selected from excessive barking, agitation, trembling, shaking, shivering, drooling, salivating, cowering and hiding, licking, scratching, yawning, clinging to owners, trying to run away, attempting to escape, soiling the place, excessive pacing and panting, refusing to eat, vomiting, whining, urinating, defecating, and any combination thereof.

8. The method according to claim 6, wherein the non-human mammal is a cat, and the behavioral stress problem is a stress sign selected from scratching, urine marking, aggression, food intake disorders, overgrooming or undergrooming, house soiling, decreased levels of activity, appearing withdrawn, or any combination of said signs.

9. A method for preventing a cat from scratching on multiple objects, said method comprising placing at least one composition according to claim 1 on an object scratched by said cat.

10. A device comprising a composition as defined in claim 1, said device comprising a means for the release of the composition of pheromones.

11. A kit comprising a device according to claim 10, and optionally a booklet providing instructions for the use of said device.

* * * * *